(12) United States Patent
Bai et al.

(10) Patent No.: US 10,444,211 B2
(45) Date of Patent: Oct. 15, 2019

(54) INTEGRATED AIR QUALITY FORECASTING

(71) Applicant: International Business Machines Corporation, Armonk, NY (US)

(72) Inventors: Xin X. Bai, Beijing (CN); Jin Dong, Beijing (CN); Hui Du, Beijing (CN); Xiao G. Rui, Beijing (CN); Xi Xia, Beijing (CN); Bao G. Xie, Beijing (CN); Wen Jun Yin, Beijing (CN); Wei Zhao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 359 days.

(21) Appl. No.: 14/980,588

(22) Filed: Dec. 28, 2015

(65) Prior Publication Data

US 2017/0184561 A1 Jun. 29, 2017

(51) Int. Cl.
*G01N 33/00* (2006.01)
*G01W 1/00* (2006.01)
*G01W 1/10* (2006.01)

(52) U.S. Cl.
CPC .......... *G01N 33/0062* (2013.01); *G01W 1/10* (2013.01); *G01N 2033/0068* (2013.01)

(58) Field of Classification Search
CPC ...... G01N 33/0062; G01N 2033/0068; G01W 1/00
See application file for complete search history.

(56) References Cited

U.S. PATENT DOCUMENTS 7,302,313 B2   11/2007  Sharp et al.
7,542,852 B1 *  6/2009  Rose ................. G01W 1/02
                                                          702/3

(Continued)

FOREIGN PATENT DOCUMENTS

CN    102647471 A       8/2012
CN    103163278    *    6/2013  ............ G01N 33/00

(Continued)

OTHER PUBLICATIONS

Zheng, Y et al., "Forecasting Fine-Grained Air Quality Based on Big Data", ACM-KDD'15, Aug. 2015, pp. 2267-2276.*

(Continued)

*Primary Examiner* — Moazzam Hossain
(74) *Attorney, Agent, or Firm* — Cahn & Samuels, LLP

(57) ABSTRACT

An embodiment of the invention provides a method where an air quality forecast having an air quality turning point is received. A processor identifies an updated air quality turning point based on weather observation information. An air quality forecast at the updated air quality turning point is generated with the weather observation information and human input, which can include human knowledge from a weather expert or an air quality expert. An air quality forecast for a first time period directly prior to the updated air quality turning point is generated with the air quality forecast at the updated air quality turning point and the human input. An air quality forecast for a second time period directly after the updated air quality turning point is generated with the air quality forecast for the first time period, the air quality forecast at the updated air quality turning point, and the human input.

10 Claims, 6 Drawing Sheets

(56) References Cited

U.S. PATENT DOCUMENTS

| | | | | |
|---|---|---|---|---|
| 2002/0144537 | A1* | 10/2002 | Sharp | G01N 1/26 73/31.01 |
| 2009/0048781 | A1* | 2/2009 | Chan | G01D 21/02 702/2 |
| 2013/0110400 | A1* | 5/2013 | Moshe | G01N 1/26 702/3 |
| 2015/0052975 | A1 | 2/2015 | Martin | |
| 2015/0212236 | A1 | 7/2015 | Haas et al. | |
| 2015/0317589 | A1* | 11/2015 | Anderson | G06Q 10/08 705/7.25 |
| 2016/0091474 | A1* | 3/2016 | Griffon | G01N 33/0036 702/24 |

FOREIGN PATENT DOCUMENTS

| | | | | |
|---|---|---|---|---|
| KR | 10-1382507 | * | 4/2014 | G06Q 60/26 |
| WO | 2014194480 | A1 | 12/2014 | |

OTHER PUBLICATIONS

Zheng et al., "Forecasting Fine-Grained Air Quality Based on Big Data," 2015 ACM, KDD '15, pp. 2267-2276.*

* cited by examiner

INTEGRATED AIR QUALITY FORECASTING

BACKGROUND

The present invention relates to systems, methods, and computer program products for integrated air quality forecasting. Weather forecasting has been performed by using a variety of different methods, such as using reports along shipping routes or using other traditional predictive methods, such as the use of almanacs. In more recent times, reports from aircraft routes, in particular the use of reconnaissance aircraft, are used to obtain information about current weather trends to forecast upcoming weather. Satellite technology, located in orbits around the Earth (e.g., Low Earth orbit (LEO), geostationary, etc.), has also enhanced the ability to obtain information and to more accurately forecast the weather by being able to view a large portion of the Earth's area at any given time.

SUMMARY OF THE INVENTION

An embodiment of the invention provides a method for predicting air quality based on human knowledge and a historical analysis. An interface can receive an air quality forecast that includes an air quality turning point. The air quality forecast prior to the turning point is above a threshold level of dissimilarity to the air quality forecast subsequent to the turning point. A processor identifies an updated air quality turning point based on weather observation information. An air quality forecast at the updated air quality turning point is generated with the weather observation information and human input. The human input includes human knowledge from a weather expert and/or an air quality expert. An air quality forecast for a first time period is generated with the air quality forecast at the updated air quality turning point and the human input. The first time period is directly prior to the updated air quality turning point. An air quality forecast for a second time period is generated with the air quality forecast for the first time period, the air quality forecast at the updated air quality turning point, and the human input. The second time period is directly subsequent to the updated air quality turning point.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system and method to integrate existing weather and air quality forecasts with human knowledge and deep insights from historical analysis. The system can generate a more accurate air quality forecast with high resolution in time. Numerical air quality forecast results, weather observations, forecast information, expert knowledge in weather, and air quality forecast, may be considered by the system, by for example, integrating such factors into a statistical model. In at least one embodiment, the system uses a numerical air quality forecast as a baseline, and uses weather observation information to forecast a turning point. A turning point is a point where the air quality curve before and after this point is very different, which may be caused by a special weather physical process. The system can evaluate the pollution at a turning point integrating expert knowledge (e.g., human expertise in weather patterns and relations between weather and air pollution). Furthermore, the system can derive a pollution curve segment between turning points. Thus, the system can improve air quality forecasts, especially in capturing the trend of air quality.

Figure 1:
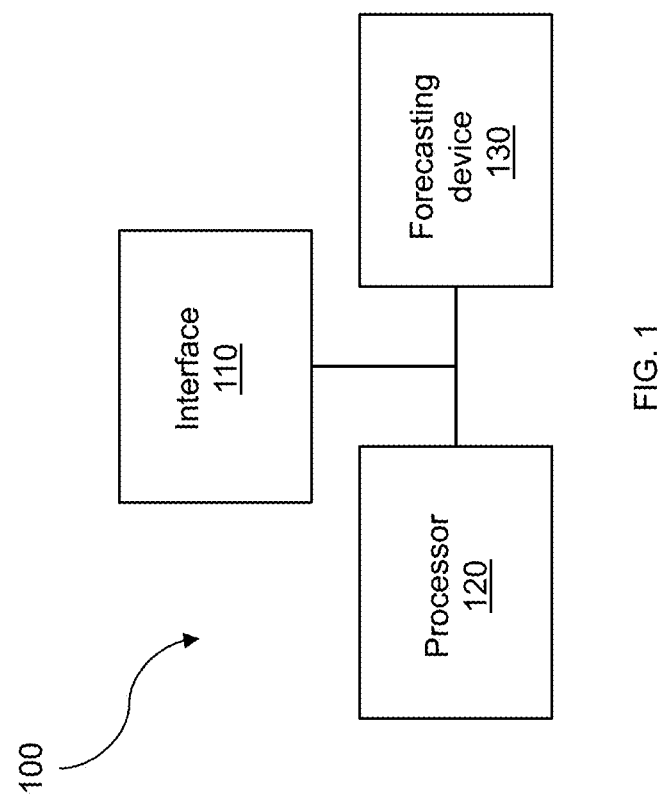
FIG. 1 is a diagram illustrating a system for predicting air quality based on human knowledge and a historical analysis according to an embodiment of the invention.
Figure 2:
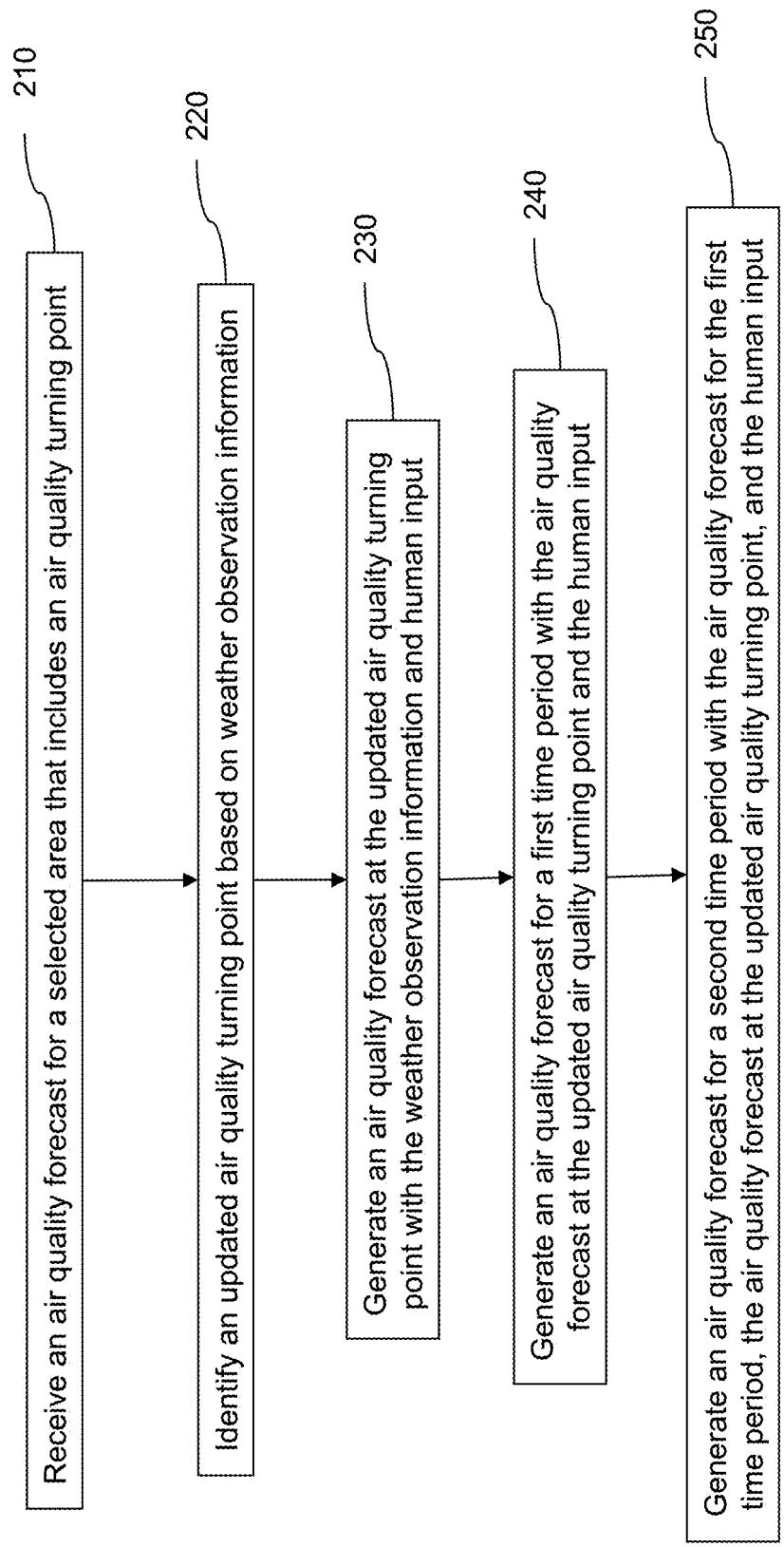
FIG. 2 is a flow diagram illustrating a method for predicting air quality based on human knowledge and a historical analysis according to an embodiment of the invention.

FIG. 1 is a diagram illustrating a system 100 for predicting air quality based on human knowledge and a historical analysis according to an embodiment of the invention. FIG. 2 is a flow diagram illustrating a method for predicting air quality based on human knowledge and a historical analysis according to an embodiment of the invention (e.g., using the system 100).

An interface 110 can receive an air quality forecast for a selected area (e.g., a large city) that includes an air quality turning point 210. In at least one embodiment, the air quality forecast prior to the turning point is above a threshold level of dissimilarity to the air quality forecast subsequent to the turning point. For example, the forecasted PM2.5 (particulate matter below 2.5 microns in diameter) is 100 before 6:33 PM and 30 after 6:33 PM. The threshold level of dissimilarity can be a change in percentage (e.g., an increase or decrease of 33% or more) and/or a change in level (e.g., an increase or decrease of 100 ppm (parts per million) or more).

A processor 120 connected to the interface 110 can identify an updated air quality turning point (different from the air quality turning point in the air quality forecast), where the updated air quality turning point is identified based on weather observation information 220. The weather observation information can include temperature, atmospheric surface pressure, wind speed, wind direction, and/or humidity. For example, the processor identifies that the PM2.5 at 6:00 PM is lower than forecasted and identifies that the updated air quality turning point is 7:12 PM.

In at least one embodiment, the processor 120 identifies an updated air quality turning point that is later in time with respect to the air quality turning point when a weather system (e.g., a cold front, a low pressure system) is forecasted to arrive at the selected area and the weather observation information indicates a delay in the arrival of the weather system to the selected area. The processor 120 can identify an updated air quality turning point that is earlier in time with respect to the air quality turning point when a weather system is forecasted to arrive at the selected area and the weather observation information indicates an arrival of the weather system to the selected area that is earlier than the forecasted arrival time.

As used herein, the term "processor" includes a computer hardware device, such as, for example, a central processing unit (CPU), a microprocessor, etc. As used herein, the term "interface" includes a computer hardware device, such as, for example, a keyboard, a mouse, a microphone, a touchpad, a touchscreen, a joystick, a controller, a camera, a disk drive, an input port, antenna, etc.

An air quality forecast at the updated air quality turning point can be generated with the weather observation information and human input 230. For example, the observations of wind speed in City X are monitored. Once the wind speed reaches 6 meters per second or higher, the observations of wind speed in City Y are monitored. When the observed wind speed reaches 6 meters per second or higher in City Y, the moving speed of a cold front can be calculated based on the distance between the two cities and the difference in time that it took the two cites to reach 6 meters per second wind speed. Once the speed of the cold front is known, the system can predict when the cold front will arrive in City Z. Because cold fronts can significantly drop the air pollution level, the turning point can be updated with a more accurate time.

Figure 5:
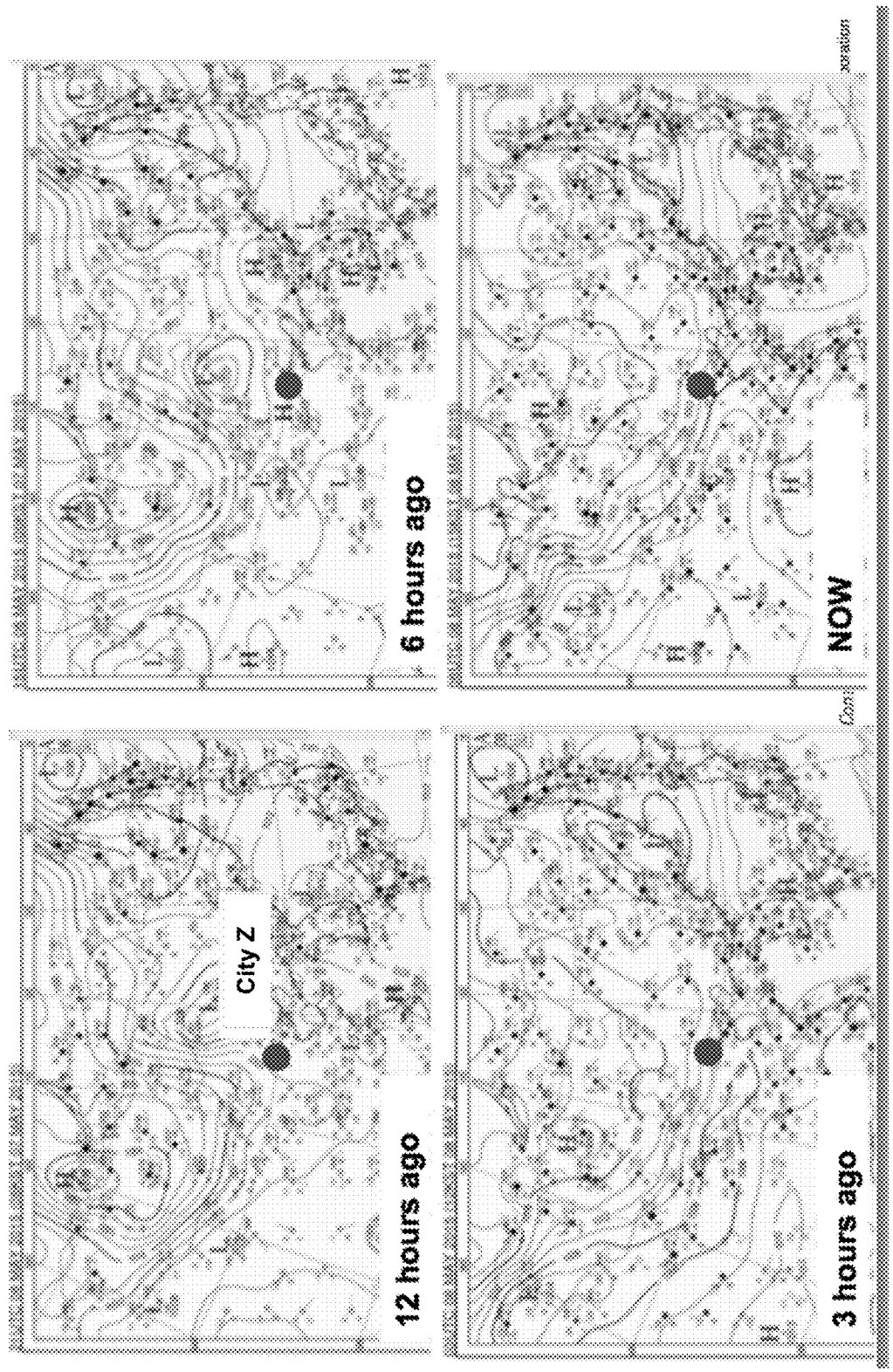
FIG. 5 illustrate maps having weather observations according to an embodiment of the invention.

The following example illustrates turning point discovery, where the turning point is the point before and after where the air quality values are very different. FIG. 5 illustrate maps having weather observations, where the large dot is the location of City Z. In the weather observation, the position and intensity of high pressure center (the top left "H" on the chart) to the northwest of City Z is an indicator based on human knowledge. The human knowledge can be integrated into the forecasting process by checking the moving speed and direction of the surface high pressure center. For example, once the high pressure moves to City Z from the north, the air quality can drop quickly in very short time (e.g., 3-5 hours). When the pressure around the City A region is more uniform (the pressure difference between different location over City A is less than 2 hPa), the air pollutants begin to accumulate, indicating an increasing trend.

The human input can include human knowledge from a weather expert and/or an air quality expert. The human input can include expert human knowledge in weather patterns and relations between weather and air pollution, terrain, and/or pollution history. In at least one embodiment, the air quality forecast at the updated air quality turning point is generated with a forecasting device 130. As used herein, the term "forecasting device" includes a computer hardware device, such as, for example, a central processing unit (CPU), a microprocessor, etc. running suitable programming to produce a weather forecast. In at least one embodiment, the forecasting device 130 is on the processor 120.

The forecasting device 130 can generate an air quality forecast for a first time period with the air quality forecast at the updated air quality turning point and the human input, where the first time period is directly prior to the updated air quality turning point (e.g., 30 minutes directly prior to the updated air quality turning point) (240). Additionally, the forecasting device 130 can generate an air quality forecast for a second time period with the air quality forecast for the first time period, the air quality forecast at the updated air quality turning point, and the human input, where the second time period is directly subsequent to the updated air quality turning point (e.g., 60 minutes directly subsequent to the turning point) (250).

In at least one embodiment of the invention, the processor 120 can identify an additional air quality turning point that is forecasted to occur subsequent to the updated air quality turning point. The forecasting device 130 can generate an air quality forecast for a third time period with the air quality forecast at the updated air quality turning point, the human input, the air quality forecast for the first time period, and/or the air quality forecast for the second time period. The third time period can be directly prior to the additional air quality turning point.

Additionally, the forecasting device 130 can generate an air quality forecast for a fourth time period with the air quality forecast at the updated air quality turning point, the human input, the air quality forecast for the first time period, the air quality forecast for the second time period, and/or the air quality forecast for the third time period. The fourth time period can be directly subsequent to the additional air quality turning point.

Figure 3:
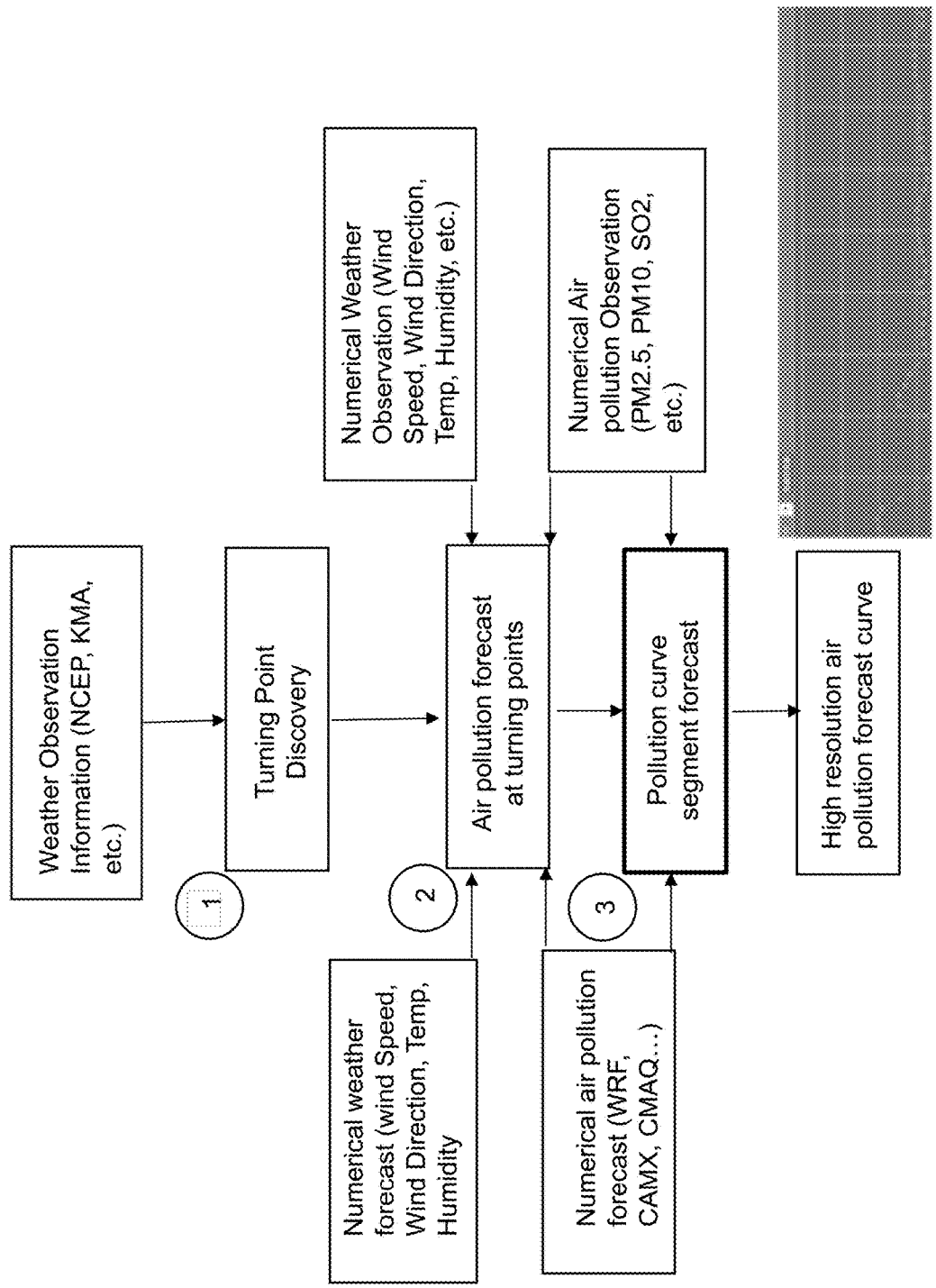
FIG. 3 is a diagram illustrating a method of generating an air quality forecast according to an embodiment of the invention.

FIG. 3 is a diagram illustrating a method of generating an air quality forecast according to an embodiment of the invention. The system can receive weather observation information and identify a turning point (1). For instance, the weather observation information can be received from a weather data source, such as the National Centers for Environmental Prediction (NCEP) and/or the Korea Meteorological Administration (KMA). The weather observation information can be based on a large scale model, which can have the advantage of capturing large weather systems for accurately identifying the turning point. The turning point can be identified by a human and/or the processor.

Figure 4:
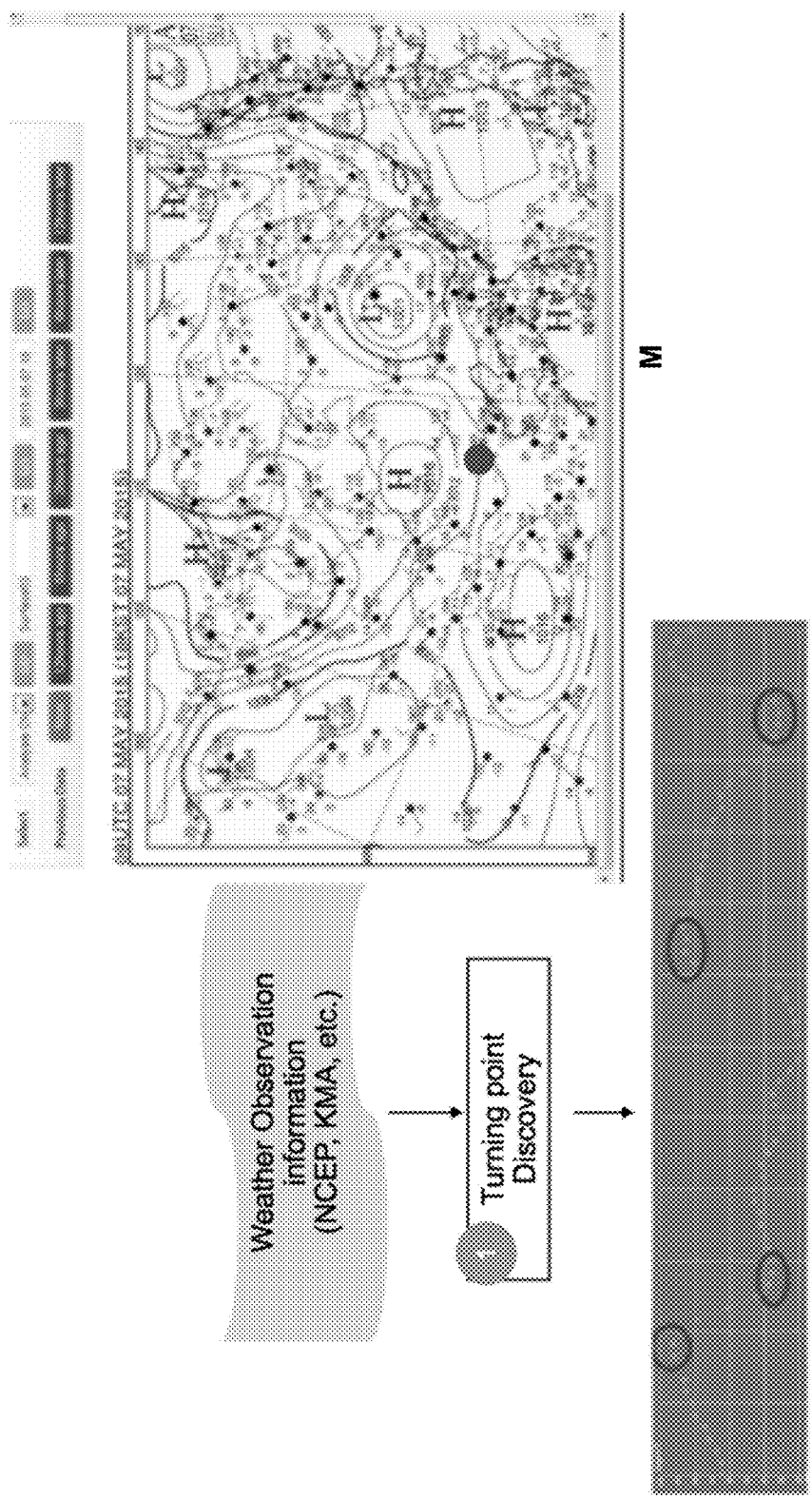
FIG. 4 illustrates the turning point discovery according to an embodiment of the invention.

FIG. 4 illustrates the turning point discovery according to an embodiment of the invention, where the turning point is the point between when the AQ values are very different. The map M on the right is the weather observation, where the position of the large dot is an indicator based on human knowledge. The human knowledge can be integrated into the forecasting process by having a processor monitor the moving speed and direction of the large dot. In at least one embodiment, the turning point occurs when the large dot approaches the target forecasting area.

The air pollution forecast can be determined at the turning point(s) ((2) in FIG. 3). More specifically, weather variables (wind speed, wind direction, relative humidity, temperature, solar radiation) from both numerical weather forecasts and numerical weather observations, a forecast from an air pollution model, and/or numerical air quality observations can be leveraged to forecast the air quality around the turning point(s). Based on this, the forecast curve can be separated into segments.

The air pollution forecast can be generated based on weather observation. For example, for heavy pollutant case (PM2.5>=150 ug/m3), the wind speed is below level 2 and the relative humidity is above 70%. Another example is that when the wind direction is south or southeast, it would more likely cause heavy pollutant.

In at least one embodiment, the system generates a high resolution air pollution forecast curve ((3) in FIG. 3). More specifically, both observational air pollution data and the forecast from the air pollution forecast model can be used for the air pollution forecast for each segment. The numerical air pollution forecast can include data from, for example in China, Weather Research and Forecasting (WRF), the Comprehensive Air Quality Model with Extensions (CAMx), and/or Mecklenburg County Air Quality (CMAQ). The observational air pollution data can include data such as PM2.5 (particulate matter below 2.5 microns in diameter), PM 10 (particulate matter 10 microns and smaller in diameter), and sulphur dioxide. Thus, the air pollution curve can be greatly improved, especially the trend.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
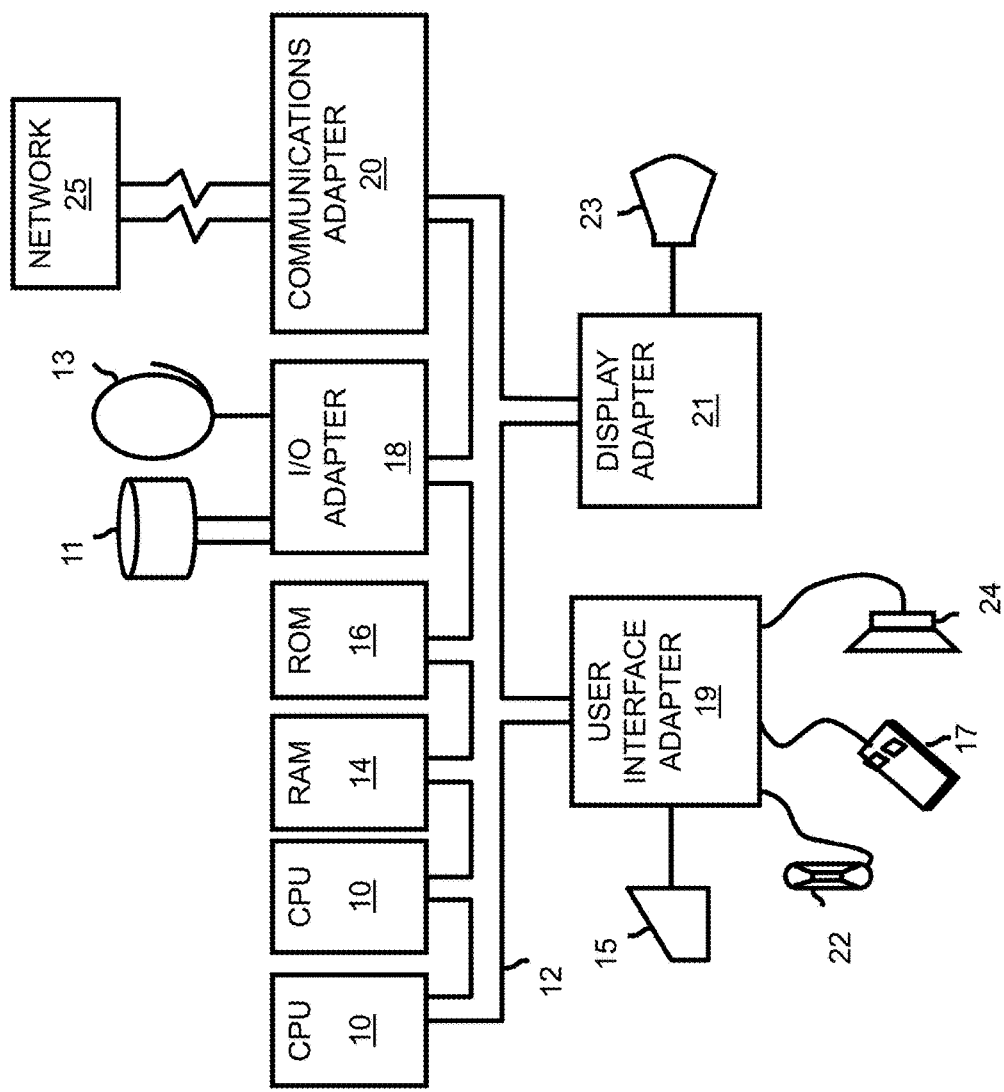
FIG. 6 is diagram illustrating a computer program product for predicting air quality based on human knowledge and a historical analysis according to an embodiment of the invention.

Referring now to FIG. 6, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for predicting air quality, comprising:
   receiving an air quality forecast for a selected area by an interface, the air quality forecast including an air quality turning point, wherein the air quality forecast prior to the turning point is above a threshold level of dissimilarity to the air quality forecast subsequent to the turning point;
   identifying an updated air quality turning point by a processor based on weather observation information including wind speed determined as a function wind speeds over a predetermined threshold from multiple measurement locations, wind direction, temperature, an atmospheric surface pressure, solar radiation, and a humidity level, wherein the weather observation information includes arrival timing of a forecasted weather system and a time at which the air quality turning point identified is based on the arrival timing of the forecasted weather system at the selected area;
   generating an air quality forecast at the updated air quality turning point with the weather observation information and received human input including a position and intensity of a weather pattern;
   generating an air quality forecast for a first time period based on the air quality forecast at the updated air quality turning point and the received human input, the first time period being prior to the updated air quality turning point;
   generating an air quality forecast for a second time period based on the air quality forecast for the first time period, the air quality forecast at the updated air quality turning point, and the received human input, the second time period being subsequent to the updated air quality turning point; and
   displaying a segmented air quality forecast curve based on the air quality forecasts around the updated air quality turning point,
   wherein the first time period is 30 minutes prior to the updated air quality turning point and wherein the second time period is 60 minutes subsequent to the updated air quality turning point.

2. The method according to claim 1, wherein said identifying of the updated air quality turning point identifies an updated air quality turning point that is later in time with respect to the air quality turning point when a weather system is forecasted to arrive at the selected area and the weather observation information indicates a delay in the arrival of the weather system to the selected area.

3. The method according to claim 1, wherein said identifying of the updated air quality turning point identifies an updated air quality turning point that is earlier in time with respect to the air quality turning point when a weather system is forecasted to arrive at the selected area and the weather observation information indicates an arrival of the weather system to the selected area that is earlier than the forecasted arrival time.

4. The method according to claim 1, further comprising:
   identifying an additional air quality turning point that is forecasted to occur after the updated air quality turning point; and
   generating an air quality forecast for a third time period with the air quality forecast at the updated air quality turning point, the received human input, the air quality forecast for the first time period, and the air quality forecast for the second time period, the third time period being directly prior to the additional air quality turning point.

5. The method according to claim 1, wherein the threshold level of dissimilarity comprises a change in air quality percentage and air quality level.

6. The method according to claim 1, further comprising:
   identifying an additional air quality turning point that is forecasted to occur after the updated air quality turning point; and
   generating an air quality forecast for a third time period with the air quality forecast at the updated air quality turning point, the received human input, the air quality forecast for the first time period, and the air quality forecast for the second time period, the third time period being directly prior to the additional air quality turning point, wherein said identifying of the updated air quality turning point identifies an updated air quality turning point that is earlier in time with respect to the air quality turning point when a weather system is forecasted to arrive at the selected area and the weather observation information indicates an arrival of the weather system to the selected area that is earlier than the forecasted arrival time, and wherein the threshold level of dissimilarity comprises a change in air quality percentage and air quality level.

7. A non-transitory computer-readable medium having computer-readable instructions stored thereon which when executed cause a computer to perform a method comprising:

receiving an air quality forecast for a selected area, the air quality forecast including an air quality turning point, wherein the air quality forecast prior to the turning point is above a threshold level of dissimilarity to the air quality forecast subsequent to the turning point;

identifying an updated air quality turning point based on weather observation information selected including wind speed determined as a function wind speeds over a predetermined threshold from multiple measurement locations, wind direction, temperature, an atmospheric surface pressure, a wind speed, a wind direction, and a humidity level, wherein the weather observation information includes arrival timing of a forecasted weather system and a time at which the air quality turning point identified is based on the arrival timing of the forecasted weather system at the selected area;

generating an air quality forecast at the updated air quality turning point with the weather observation information and received human input including position and intensity of a weather pattern;

generating an air quality forecast for a first time period based on the air quality forecast at the updated air quality turning point and the received human input, the first time period being prior to the updated air quality turning point;

generating an air quality forecast for a second time period based on the air quality forecast for the first time period, the air quality forecast at the updated air quality turning point, and the received human input, the second time period being subsequent to the updated air quality turning point; and displaying a segmented air quality forecast curve based on the air quality forecasts around the updated air quality turning point.

8. The non-transitory computer-readable medium according to claim 7, wherein the received human input includes relations between weather and air pollution, terrain, and pollution history.

9. The method according to claim 1, wherein the threshold level of dissimilarity comprises a change in air quality percentage or air quality level.

10. A device for predicting air quality, comprising:

processing circuitry configured to receive an air quality forecast for a selected area by an interface, the air quality forecast including an air quality turning point, wherein the air quality forecast prior to the turning point is above a threshold level of dissimilarity to the air quality forecast subsequent to the turning point, identify an updated air quality turning point by a processor based on weather observation information including wind speed determined as a function wind speeds over a predetermined threshold from multiple measurement locations, wind direction, temperature, an atmospheric surface pressure, solar radiation, and a humidity level, wherein the weather observation information includes arrival timing of a forecasted weather system and a time at which the air quality turning point identified is based on the arrival timing of the forecasted weather system at the selected area, generate an air quality forecast at the updated air quality turning point with the weather observation information and received human input including a position and intensity of a weather pattern, generate an air quality forecast for a first time period based on the air quality forecast at the updated air quality turning point and the received human input, the first time period being prior to the updated air quality turning point, generate an air quality forecast for a second time period based on the air quality forecast for the first time period, the air quality forecast at the updated air quality turning point, and the received human input, the second time period being subsequent to the updated air quality turning point, and display a segmented air quality forecast curve based on the air quality forecasts around the updated air quality turning point, wherein the first time period is 30 minutes prior to the updated air quality turning point and wherein the second time period is 60 minutes subsequent to the updated air quality turning point.

* * * * *